United States Patent [19]
Schlicht et al.

[11] 3,975,387
[45] Aug. 17, 1976

[54] REMOVAL OF UNCONSUMED REACTANTS AND POLAR BY-PRODUCTS FROM REACTION PRODUCT MIXTURES THROUGH ADSORPTION ON POLYURETHANE FOAM

[75] Inventors: Raymond C. Schlicht, Fishkill; Frederic C. McCoy, Beacon, both of N.Y.

[73] Assignee: Texaco Inc., New York, N.Y.

[22] Filed: Feb. 6, 1974

[21] Appl. No.: 440,096

[52] U.S. Cl. .............. 260/247.5 R; 260/268 R; 260/583 N; 260/583 P; 260/584 B; 260/561 R; 252/50; 252/51.5 R; 252/51.5 A
[51] Int. Cl.² .............. C07C 85/26; C07C 91/10; C07D 295/12
[58] Field of Search ............ 260/247.5 R, 583 N, 260/583 P, 561 R, 584 B, 268 R; 252/50

[56] References Cited
UNITED STATES PATENTS

| | | | |
|---|---|---|---|
| 3,406,204 | 10/1968 | Bathellier | 260/583 N |
| 3,617,531 | 11/1971 | Schlicht | 208/263 |
| 3,751,475 | 8/1973 | Van der Voort | 260/583 P |
| 3,787,497 | 1/1974 | Hellmuth | 260/583 N |

FOREIGN PATENTS OR APPLICATIONS

| | | | |
|---|---|---|---|
| 2,004,314 | 10/1970 | Germany | 208/263 |

*Primary Examiner*—Lorraine A. Weinberger
*Assistant Examiner*—Michael Shippen
*Attorney, Agent, or Firm*—T. H. Whaley; C. G. Ries; Robert A. Kulason

[57] ABSTRACT

Separation of unreacted amines and other undesired by-products from amine-derived dispersants and additives through adsorption of the undesired amines and by-products on polyurethane foam.

14 Claims, No Drawings

REMOVAL OF UNCONSUMED REACTANTS AND POLAR BY-PRODUCTS FROM REACTION PRODUCT MIXTURES THROUGH ADSORPTION ON POLYURETHANE FOAM

BACKGROUND OF INVENTION

In the preparation of dispersants and additives incorporating amine reaction products for use in lubricants and fuels, unconsumed reactant amines and by-products, in the form of alkenyl amines and the like are usually present. Even in minute quantities, these impurities adversely affect the performance of the dispersants or additives as well as causing a hazy cast in their appearance; often, an undesired coloration, and color-instability.

Illustrative of the adverse effects secured where these low molecular weight reactants and byproducts are permitted to remain in the dispersant is their tendency to form deposits about the lower piston skirts as reflected particularly by Caterpillar diesel engine tests.

Various means for removal of these undesired reactants and byproducts, occurring primarily in the form of alkenyl amines have been known heretofore, including high vacuum distillation, solvent extraction techniques and the like.

Use of the foregoing methods of separation involve substantial difficulties and the incurring of substantial liabilities, as for example, the need for elaborate equipment, low throughput, and substantial expense. In addition, the removal effected is often not complete and hence the elimination of engine deposits is not satisfactorily resolved.

The use of an inexpensive and simple technique has been described heretofore for application to the removal of phenolic materials from phenol-derived solutions in which polyurethane foam provides an adsorbent for the undesired phenolic materials but the application of this process to removal of amines and particularly alkenyl amines, often in extremely small amounts, from amine-based dispersants and additives has not been elucidated.

Thus, if polyurethane foams could be used in securing amine-based lubricants and additives free of low-molecular weight unreacted amines and amine by-products, a significant advance in the state of the art would be achieved.

SUMMARY OF INVENTION

It is therefore a general object of the invention to provide an efficient, inexpensive means for treating amine-based additives and dispersants to eliminate therefrom undesired unconsumed amine reactants and byproducts.

It is a further objective of the invention to provide amine-based additives and dispersants for lubricants and fuels substantially free of the detrimental effects to performance, and substantially free, as well, of undesired haze, color, and tendencies to oxidative and color instability, inherent in these products when unreacted amine components and byproducts, even in trace amounts, are not removed therefrom prior to use.

Other objects and advantages of this invention will become evident from the following description.

Accordingly, it has now been discovered that alkylene and polyalkylene polyamines and other low molecular weight amine byproducts resulting from reaction of polyolefins, and in particular, halogen-substituted, nitrated or nitrooxidized polyolefins, or substituted succinic acids, succinic anhydrides and derivatives (including halogen-substituted succinic derivatives) thereof, with alkylene or polyalkylene polyamine are conveniently recovered by contacting the reaction product mixture with polyurethane foam.

The finished products, from which the low molecular weight byproducts and unreacted amines are removed by adsorption on the foam, are amine derivatives having high molecular weight polyalkenyl groups constituting, illustratively, valuable fuel and lubricant dispersant additives.

The adsorption process of the invention is both simple and inexpensive.

DETAILED DESCRIPTION OF THE INVENTION

The process of this invention comprises therefore contacting polyurethane foam with alkenyl amine (including alkenyl polyamines) resulting from the reaction of a polyolefin (including polymeric diolefins), a halogenated, and particularly a brominated or most desirable a chlorinated, nitrated or nitroxidized polymeric olefin or diolefin, a halogenated or unsubstituted alkenyl succinic anhydride, their corresponding acids or the lactone-succinic acid derivative of said anhydride or anhydride derivative with, preferably, an amine selected from the formula:

Formula I: 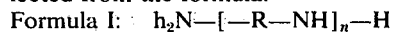

wherein R is an alkylene radical of from about 2 to 8 carbon atoms and $n$ is an integer of from about 1 to 6; or with an ethoxylated or propoxylated mono-amine; or with an ethoxylated or propoxylated di- or poly-amine which has 1 to $n+4$ hydroxy alkyl groups substituted for 1 to $n+4$ hydrogen atoms of the NH or $NH_2$ groups of an amine of Formula I structure; or such heterocyclic amines as illustratively bis-aminoethylpiperazine, aminoethyl morpholine, and N-beta-hydroxyethyl-4-(3-hydroxypropyl)piperazine, for a period of time sufficient to effect adsorption on the foam of substantial portions of said unreacted amines or byproducts of high nitrogen content and having a molecular weight of less than about 500 as contrasted with the desired higher molecular weight polyalkenyl polyamines produced by the foregoing reaction. Prior to such contact the foregoing reaction product is diluted with a hydrocarbon solvent. The polyurethane foam is readily regenerated by application thereto of a polar organic solvent.

Illustrative of the preferred amine reactants are tetraethylenepentamine, pentaethylenehexamine and 1,4-hexanediamine, as well as ethylenediamine, propylenediamine, butylenediamine, hexylenediamine, diethylenetriamine, triethylenetetramine, dipropylenetriamine, dihexylenetriamine and also, though somewhat less preferred, ethoxylated and propoxylated mono-, di- and polyamines, for example, diethanol amine, and generally those products derived from the reaction of ammonia with propylene oxide, ethylene oxide and the like.

In respect to the second reactant, i.e., the reactant which reacts with the aforementioned amine reactant to form a derivative to be treated with polyurethane foam in accordance with the method of the invention, one group of preferred materials in terms of dispersant produced upon reaction, particularly with the foregoing preferred amine reactants, and the facility with which it has been established that unreacted amine and amine by-product are removed from the reaction product dispersant according to the practice of the invention, is a nitrated, nitroxidized or halogenated polyolefin of from 30 to 200 carbon atoms secured by polymerization by standard means of an alkene of 2 to 5 carbon atoms, and exemplified by ethylene, propylene, 1-butene, 2-butene, isobutene and mixtures thereof. A particularly preferred olefinic reactant within the foregoing molecular weight ranges are polybutenes and specifically halogenated polyisobutenes which are composed, as available commercially, of high molecular weight monoolefins, normally present in a range of about 85 to 98 wt. %, the balance comprising isoparaffins, and having a viscosity at 210°F. of 627 to 675 cs. as determined by ASTM D445.

Other suitable and illustrative second reactants are the mono-, di-, or higher, consubstituted halogen-substituted nitrated or nitooxidized products of olefins such as alpha-olefins, cracked oil fractions, polyethylenes, polypentenes, polyhexenes and the like, as well as mixed polymers including, by way of illustration, ethylene-propylene, ethylene-butylene and propylene-butylene, copolymers, as well as the diene copolymers such as poly-butadienes, polyisoprene, copolymers of dienes with mono-olefins and the like.

Illustrative of the most preferred embodiments of the alkenyl amine reaction product mixtures constituting the additives and dispersants subject to the practice herein described are those crude products secured from the reaction of polybutenes which are substantially monochlorinated, or nitric acid oxidized, having in either case, an average molecular weight of about 1200, with the polyamine, tetraethylenepentamine, or preferably pentaethylenehexamine. The polybutene reactant is a polymer usually and conveniently also derived from a mixture of butene isomers. The reaction product prepared by amination of an HNO₃ "oxidized" polyolefin may be illustrated by the following sequence, although other types of oxidate/amine reactions may also occur:

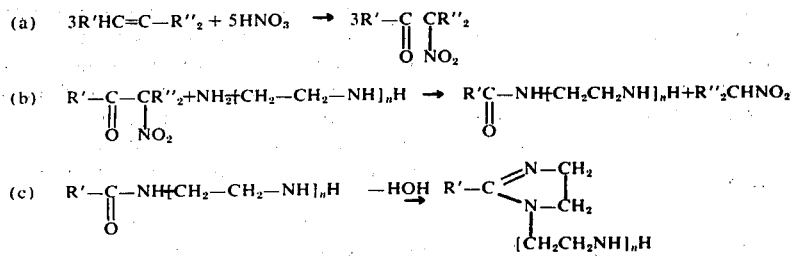

In this sequence, the symbol $n$ has the values assigned with respect to Formula I above and R' and R'' comprise the various alkyl groups present in the polybutene moiety. The reaction (c) will only occur where a di- or polyamine such as one encompassed by Formula I is employed.

Still further examples of the aforedescribed second reactants are alkenyl succinic anhydride, alkenyl succinic acid or lactone-acid derivative prepared from the foregoing anhydride. The alkenyl moieties present in each of the foregoing succinic anhydrides and derivatives thereof are the olefinic radicals derived from the unsubstituted or halogenated olefins described hereinabove. Typically, the additives and dispersants prepared upon reaction of the alkenyl succinic anhydrides or acids with the foregoing amines, e.g. those of Formula I above, are the corresponding alkenyl succinimides.

An effective dispersant subject to treatment according to the practice of the invention is that resulting from mixing a substituted succinic compound selected from the formula:

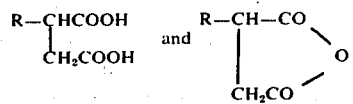

wherein R is a substantially aliphatic hydrocarbon radical having from about 50 to 200 carbon atoms with at least about one-half of a molar equivalent amount of a polyethylene polyamine and, in the case of the acid, heating the resultant mixture to effect acylation and remove the water formed thereby. The anhydride, however, may react without external heating and hence may optionally be heated to complete reaction or improve handling, if further reactions of the intermediate amic acid are desired. Suitable amines are diethylenetriamine, triethylenetetramine, tetraethylenepentamine and amino alkylated heterocyclic compounds. The reaction involves amidation of a dicarboxylic acid or anhydride thereof with a polymer to produce amino-substituted acyclic diamides, amic acids, polymeric amides, or a combination of these types of products. It will be noted that the amide groups may further react to form imide groups in the process.

The term "equivalent" as employed in the preceding paragraph means that a minimum of one-half mole of alkenylsuccinic anhydride or acid per mole of amine is required. This is the least amount of acid which can react with all of the amine added (via amic acid or acyclic polyamide formation). The maximum amount of acid or anhydride possible to react is one-half mole per primary or secondary amino group. Generally, one or two moles of acid or anhydride per mole of amine, regardless of the total number of nitrogen atoms, is preferred. The reaction product is effective in amounts ranging from about 0.25 to 20.0 wt. %. Methods for preparing the polyethylene polyamine reaction products are well known and have been described in U.S. Pat. Nos. 3,131,150 and 3,172,892.

Suitable dispersants for treatment according to the practice of the invention and derived from the reaction of heterocyclic amines and particularly piperazines and piperidines with alkenyl succinic anhydrides appear in U.S. Pat. Nos. 3,424,684 and 3,630,903 respectively.

To effect removal of the undesired, unconsumed reactant amine and any amine by-product having a molecular weight of less than 500 from the reaction products providing the dispersants and additives being treated pursuant to this invention, the foregoing reaction products are first incorporated in the hydrocarbon solvent in a volume ratio within the range of 1:1 to 1:3, and most desirably about 1:2, respectively. Examples of suitable solvents are low molecular weight saturated aliphatic cycloaliphatic and aromatic hydrocarbons, of which the saturated straight and branch-chain aliphatic hydrocarbons, containing 3 to 8 carbons, are preferred for use herein. Cycloaliphatic hydrocarbons containing from 3 to 8 carbon atoms and those aromatic hydrocarbons of from about 6 to 9 carbon atoms including the alkyl substituted derivatives thereof are also useful as diluents in the practice herein described.

Of the foregoing solvents employed as diluents herein n-heptane, hexane and n-octane are also very desirable and solvents such as 2-methyl propane, 2-ethyl hexane, nonane, decane, undecane, cyclo-propane, cyclohexane, and cycloheptane are also considered very useful. Less preferred generally but entirely functional for the purpose of this invention are benzene, and the methyl-substituted derivatives thereof, for example, toluene and ortho-, meta-, and paraxylene, as well as mixtures thereof.

The foregoing solvents, and particular n-heptane, are readily stripped from the recovered amine product by conventional means well known to those skilled in the art.

The adsorbent polyurethanes may be flexible (including high resilience types), or rigid polyester or polyether urethane foam of the so-called reticulated type described in U.S. Pat. No. 3,170,820, or of the conventional open celled variety. Microcellular foams are operative as well. The flexible open-cell or, even more desirably, the flexible, reticulated polyurethane foams are preferred. Significantly less preferred, although functional, are the substantially more closed cell types of foam. Reticulation assures a larger surface area for adsorption. In addition, polyether urethane foam with lower nitrogen content and corresponding higher ether oxygen content provide generally more effective absorbents.

However, the foam can in any event be conveniently shredded or otherwise subdivided, by any convenient and conventional technique for packing the adsorption column. A Waring blender has been found to provide a good means for shredding of the foam by way of illustration. Where the shredding of flexible foam is being undertaken, it is desirable additionally to do so at a reduced temperature, for example, 0°C. to 20°C., so that the foam will be sustained in a comparatively rigid state and thus more susceptible to comminution. A convenient means for accomplishing this is the inclusion of ice and water in the blender during the shredding operation.

The size of the polyurethane particles in the shredded or comminuted state is not narrowly critical but generally a mesh size of 1 to 50 (and most desirably about 1–15) is preferred. Also the foam may be synthesized in situ to completely fill the adsorption section of the apparatus to be used and then rendered into a reticulated cell form for use in the subject process.

Further illustrative of polyester urethane and polyether urethane foams useful in the practice of the invention, their formulation and conventional methods of preparation are those described in Saunders, J. H. and Frish, K. C., *Polyurethanes: Chemistry and Technology 1. Chemistry* (High Polymers, Volume XVI) Interscience Publishers, New York 4th printing 1967, pgs. 32 to 48 inclusive; and Bruins P. F., *Polyurethane Technology*, Interscience Publishers, 1969, pgs. 40 to 63, 78 to 86, 104 to 116.

It has been found that the polyurethane foams can adsorb, particularly where the reticulated flexible foams are utilized, unreacted amines and low-molecular weight amine-containing byproducts referred to elsewhere herein in amounts by weight approximately equal to the weight of the foam itself. This is in favorable contrast to other solid absorbents which are materially less effective on a comparable weight basis as well as on the basis of comparable cost.

The polyurethane foam may be desirable intermixed after shredding with a filler, and preferably a cellulosic material, of substantially identical mesh size in a ratio preferably of 0.5 to 1.0 parts respectively. Illustrative celluloses for use herein are carboxy methyl cellulose, hydroxy ethyl cellulose and methyl cellulose. The cellulose is substantially inert to the adsorptive process described herein but provides wettability to the adsorbent composition and inhibits channelling within the foam column, as well, and thereby may add to the adsorptive effectiveness of the foam.

Regeneration of the polyurethane adsorbent is readily effected, as indicated above, with low-boiling polar slvents, including for example, methyl ethyl ketone, tetrahydrofuran, diethyl ether and low molecular weight chlorinated hydrocarbons and alcohols, particularly saturated aliphatic alcohols containing from about one to six carbons. Methanol is particularly preferred as the most efficient of these regenerative solvents.

These solvents do not injure the foam and hence, as indicated above, the cycle of adsorption and regeneration can be repeated indefinitely. The solvents used both in adsorption and regeneration are as a result very economic to use. Thus the adsorption and regeneration processes of the invention represent a considerable improvement over ion exchange resins or other solid adsorbents for additional reasons of economy as well as simplicity.

Adsorption occurs effectively within the range of about −20°C. to about 50°C. Preferred temperatures are within the range of 20°C. to 30°C. and most desirably and conveniently about 25°C.

The separation process of the invention is conducted by passing the amine reaction product in the foregoing solvent in a liquid phase through a column packed with the adsorbent foam and such filler as may be additionally included. The diluted additive may be percolated either upward or downward through the packed column.

The efficiency of the adsorptive process is conveniently monitored by analysis of the recovered eluate for low molecular weight material. Ultimately, the adsorbent becomes saturated to a point where the content of unreacted amine and undesired low molecular weight amine byproduct in the eluate recovered from the column is approximately the same as that of the charged reaction product mixture if the adsorbent is not earlier replaced or regenerated at any time that the unconsumed amine and undesired amine byproduct contents exceed designated maximum values.

It will be apparent that the operation can be performed as a batch or continuous process. In either event, it is most convenient to effect regeneration of the foam by periodic interruption of the adsorption process in order to contact the adsorbent foam with regenerative solvent; most desirably, as indicated above, methanol, which is simply percolated through the packed column. If desired, the column may be air dried thereafter to remove any trace of solvent remaining. In the latter event particularly, it is desirable to substitute a second column in the separation step if it is desired to continue the adsorption process without material interruption while the packed foam of the original column is being regenerated.

The following examples are further illustrative of the invention.

EXAMPLE I

This example illustrates the adsorptive activity of polyurethane foam where contacted with a dispersant prepared by reaction of a polyalkyleneamine with a polybutene previously subjected to oxidation with nitric acid.

A polybutene prepared from a mixture of butene isomers having a molecular weight of about 1200 (Amoco INDOPOL H-300 polybutene) was reacted with nitric acid in a mole ratio of acid to olefin of 2:1. The reaction was carried out at about 180°F. for a period of 11 hours. The reaction was permitted to continue thereafter for a further period of 8 hours at 215°F. The resulting nitric acid oxidate was subjected to extraction and stripping with heptane and methanol and was then reacted with tetraethylene pentamine in a mole ratio of saponifiable oxidate to amine of 1:2 and in an amount sufficient to formulate 250 grams of crude liquid dispersant product. The reaction was undertaken at a temperature of 350°F. to 370°F. for a period of twelve hours in a solution containing 10% of xylene. The crude dispersant was filtered to remove solid byproducts and contained at least 0.8 wt. % of free amine (3.1% nitrogen as against 2.8% calculated for an amine-free product at an assigned 100% conversion of the oxidation). The crude dispersant was added to 700 milliliters (ml) of heptane and was introduced into a glass column having an inside diameter of 5 cenitmeters and a length of about 70 centimeters. The column was packed with about 11.2 grams of a comminuted open cell polyester urethane (Nopco "Ester-type" foam) and about 5.6 grams of shredded hydrophilic cellulose. The foregoing dispersant and diluent percolated through the vertically aligned column at ambient temperature (about 77°F.), after which 200 ml. more heptane was percolated through the column. The recovered eluate (after removing the heptane in vacuo) was 221 grams or 88.4 percent of the amount of dispersant oil introduced into the column, and evidenced the following values: percentage nitrogen found: 2.5; nitrogen material balance: 71 percent of charged nitrogen by weight. The percolation thus provided a treated product reduced in nitrogen content. The foam was teated with 400 ml of methanol which was percolated through the column in the same manner as the crude dispersant oil and heptane diluent and resulted in recovery from the foam of 14 grams of adsorbed product or 5.6 percent of the total dispersant charged. The adsorbed product thus recovered manifested the following characteristics: percentage of nitrogen found: 15.0; nitrogen material balance: 27 percent of charged nitrogen by weight. The methanol eluate also evidenced a low molecular weight and high nitrogen content which was identified by infra-red analysis to be a mixture of unreacted polyamine and low molecular weight, i.e. less than 500, amine-reaction byproducts. At the same time, the absence of free amine from the dispersant which percolated through the foam was made evident by turbidity studies comparing oil blends of the treated and untreated amine. According to the test procedure very small amounts, typically 0.05 percent by weight of polyamine in an amine dispersant oil, produce a haze in oil blends, largely due to interaction of the polyamine with a mixture of zinc dialkyldithiophosphates, wherein the alkyl moieties contain from 3 to 6 carbons, present in commercially available lubricant oil blend, which also contains, inter alia, calcium sulfonate, and a standard methacrylate pour point depressant. The phosphate and methacrylate incorporated in the olefinic amine reaction product in amount by weight of said reaction product of 1.5 wt. % of phosphate and 0.5 wt. % methacrylate respectively. The untreated, crude amine dispersant gave a percentage turbidity upon reaction with dialkyldithiophosphate of 92.3 percent (out of 100 percent maximum possible value), while the oil blend of the treated dispersant was reduced in turbidity to 7.8 percent, an amount essentially undetectable by the human eye.

EXAMPLE II

This example illustrates the practice of the invention with a crude dispersant similar to that of Example I but which contains relatively little free amine.

The procedure employed was similar to that of Example I. The crude dispersant employed and prepared as described in Example I was the product of a reaction in a 1 to 1 mole ratio of amine to $HNO_3$-oxidized polybutene. This resulted in a crude dispersant for introduction into the foam packed column of Example I (which had been regenerated by the methanol treatment described therein followed by air-drying) containing a total of 1.3% N which includes very reduced amounts of unreacted amine as evidenced by a percentage of turbidity of an oil blend of the untreated additive of only 6.5 percent using the Lumetron Turbidity Test of Example I. The crude dispersant was mixed with heptane diluent before introduction in proportions of 148 grams of dispersant to 180 ml. of heptane. Elution was undertaken with an additional 200 ml. of heptane. The foregoing mixture was inroduced into the identical column packed with the regenerated polyester type polyurethane foam of Example I and percolated therethrough at about 77°F. The recovered eluate which flowed from the column was found (after removal of solvent in vacuo) to constitute 98 wt. % of the charged dispersant containing 1.1 wt. % nitrogen, a nitrogen material balance of 75 percent of the charged weight of nitrogen, and a 6.0 percent turbidity of its oil blend after percolation as measured by the Lumetron Turbidity Test of Example I.

The used foam present in the column was regenerated using 300 ml of methanol and thereby recovered from the foam was the adsorbed free amine and low molecular weight amine by-products in an amount of 3 grams or 2 percent of the charged crude dispersant. This recovered free amine and low molecular weight by-product was characterized by a content of 18 percent nitrogen and a nitrogen material balance of 25 percent of charged nitrogen by weight.

Although the foam-adsorbed material was less in contrast to Example I, the methanol-eluted matter had a higher nitrogen content and the recovered dispersant, a reduced nitrogen content, evidencing the functionality of the practice of the invention even where only small amounts of unreacted amine are present in the crude product submitted for treatment. This example also indicates the facility with which the polyurethane foam is regenerated by polar solvent since the same foam used in Example I was used effectively in the recovery procedure of this example.

EXAMPLE III

This example illustrates the separation and recovery process of the invention with a different amine dispersant.

A chlorinated polybutene prepared from a mixture of butene isomers and having a molecular weight of about 1200 (Amoco INDOPOL H-300) was reacted with 1,4-hexanediamine in the presence of sodium hydroxide. The product underwent filtration to remove sodium chloride and vacuum stripping so that the test procedure could be assessed with reduced amounts of free amine present in the crude dispersant to be treated by the practice of the invention. Gas chromatographic analysis indicated the crude amine dispersant contained about 0.2 wt. % of free amine and a percentage by weight of 0.69 of total nitrogen. The column employed was similar to that of Examples I and II and contained 30 grams of the same kind of polyester foam and the same proportion of hydrophilic cellulose. An initial solution of the crude dispersant was admixed with 800 ml of heptane. The foregoing mixture was introduced into the column and the column was then eluted with another 500 ml heptane. The heptane eluate was split at the point where eluate color became significantly darker. The first portion of 800 ml. of heptane eluate was found to contain 0.63 percent of nitrogen; and had a nitrogen material balance of 90 wt. % of the charged nitrogen. This first portion comprised (after stripping solvent in vacuo) 198 grams of recovered dispersant or 99 percent of the crude product charged. The last 500 ml. of heptane eluate contained after removal of solvent, 15.2 percent nitrogen. The adsorptive capacity of the foam was approaching exhaustion at this point. This second portion contained only 0.5 gram of charged dispersant and its nitrogen material balance was 6.4 percent of the charged nitrogen by weight.

The foam was next treated with methanol (500 ml.) and the eluate vacuum stripped, thereby 0.44 grams (0.2 wt. % of the dispersant charged) was recovered from the foam. The percentage of nitrogen of this recovered product was 10.9% for a nitrogen material balance of 3.5% of the charged nitrogen by weight. Blending the dispersants at 5% active wt. into an oil as in Example I, the percentage turbidity using the crude dispersant was 11.5% as contrasted with 4.5% using the major fraction of the heptane eluted dispersant, as measured by the Lumetron Turbidity Test.

The heptane is readily removed by conventional means from the recovered dispersant. The effectiveness of the adsorptive procedure of the invention is again evident as reflected by the results secured in the foregoing example. It is noted that the percolated oil recovered in the foregoing examples evidenced better color and greater oxidative and color stability than the crude dispersant oils charged to the treatment column.

It will be evident that the terms and expressions which have been employed are used as terms of description and not of limitation. There is no intention in the use of such terms and expressions of excluding equivalents of the features shown and described or portions thereof and it is recognized that various modifications are possible within the scope of the invention claimed.

We claim:

1. In the separation and recovery of unreacted amines and amine reaction by-products having a molecular weight of less than about 500 from the reaction of an olefinic-containing reactant selected from an unsubstituted, nitrated, nitro-oxidized or halogenated polymeric monoolefin; an unsubstituted, halogenated or nitrooxidized polymeric di-olefin; a halogenated, nitrated or nitrooxidized copolymer of said mono and di-olefins; a halogenated or unsubstituted alkenyl succinic acid, succinic anhydride or the lactone-acid derivatives thereof; said halogenated or unsubstituted alkenyl moiety in each of said succinic acid, succinic anhydride and lactone-acid derivatives being a radical selected from a corresponding polymeric olefin, diolefin or copolymer thereof; and an amine reactant selected from (a) an alkylene amine of the formula:

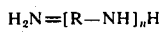

wherein R is an alkylene radical of from about 2 to about 8 carbon atoms and $n$ is an integer of from about 1 to about 6, (b) an ethoxylated amine, (c) a propoxylated mono-, di-, or polyamine, (d) an amino substituted piperazine, or (e) an amino substituted morpholine, the steps that comprise forming a solution of said reaction product with a hydrocarbon solvent and contacting said solution with polyurethane foam for a period of time sufficient to permit adsorption by said foam of a substantial portion of said unreacted amine and amine byproduct.

2. The process of claim 1 wherein said olefinic reactant is a chlorinated polybutene having a molecular weight of from about 500 to about 50,000.

3. The process of claim 1 wherein said olefinic reactant is a nitro-oxidized polybutene having a molecular weight of about 500 to 50,000.

4. The process of claim 3 wherein said olefin reactant is derived from a polybutene having a molecular weight of from about 1000 to 2000.

5. The process of claim 1 wherein said amine reactant is an amine of the formula:

wherein R is an alkylene radical of from about 2 to about 8 carbon atoms and $n$ is an integer of from about 1 to about 6.

6. The process of claim 5 wherein said amine is tetraethylene pentamine.

7. The process of claim 5 wherein said amine is 1,4-hexanediamine.

8. The process of claim 1 wherein said amine reactant is the reaction product of one to three molar proportions of propylene oxide to ammonia.

9. The process of claim 1 wherein said amine reactant is the reaction product of 1 to 3 molar proportions of ethylene oxide to ammonia.

10. The process of claim 1 wherein said amine reactant is bis-aminoethyl piperazine.

11. The process of claim 1 wherein said amine reactant is aminoethyl morpholine.

12. The process of claim 1 wherein said hydrocarbon solvent is a saturated aliphatic hydrocarbon containing from about 1 to about 10 carbons.

13. The process of claim 1 wherein said solvent is heptane.

14. The process of claim 1 wherein said amine reactant and olefinic reactant are reacted in at least equimolar proportions of amine to olefinic-containing reactant.

* * * * *